ated by using the tubular teeth of the invention for the replacement of the lateral teeth. A casting pattern is made by fastening in a wax baseplate—in addition to standard-size frontal teeth—longitudinally perforated hollow lateral teeth which are anatomically true on their outside. These tubular teeth are now completely filled with wax and the pattern is placed into an articulator together with the opposite denture and the superfluous wax is removed from the top of the teeth by motion of the articulator in a conventional manner. The smoothed-down pattern is placed into the patient's mouth for final adjustment and is then used for making a casting mold. After melting the wax out of the baseplate and the tubular teeth, the mold is filled with a plastic material in liquid stage which also fills the tubular teeth up to their upper surfaces. The denture is now ready and does not require additional fitting and grinding in the patient's mouth.

United States Patent [19]

Laszlo

[11] Patent Number: 4,608,020
[45] Date of Patent: Aug. 26, 1986

[54] METHOD OF MAKING REMOVABLE DENTURES

[76] Inventor: Kalman Laszlo, 18/2 Marseille Street, Kiriat Sprinzak, Haifa, Israel

[21] Appl. No.: 611,989

[22] Filed: May 18, 1984

[51] Int. Cl.4 ............................................. A61C 11/00
[52] U.S. Cl. ..................................... 433/213; 433/167
[58] Field of Search ........................ 433/213, 167, 171

[56] References Cited

U.S. PATENT DOCUMENTS 833,883 10/1906 Lentz ................................. 433/213
3,644,996 2/1972 Weinkle ............................. 433/171

Primary Examiner—John J. Wilson
Attorney, Agent, or Firm—Robert J. Koch

[57] ABSTRACT

The time for making artificial dentures is much short-

5 Claims, 4 Drawing Figures

METHOD OF MAKING REMOVABLE DENTURES

The invention relates to the making of partial or complete artificial dentures, more particularly to the forming of the lateral teeth in dentures destined either for the upper or the lower jaw.

Dentures are either partial or complete, the former being used when some teeth are present in the jaw, and the latter when all teeth are missing. Both types have been known since the 17th century, but is was only in the beginning of the 19th century that dentures were produced which were held by close adaptation to the gums in the mouth cavity. Lower jaw dentures are generally in the shape of a horseshoe, while the upper denture usually extends over a large part of the upper palate. Proper fit of a denture requires making an exact impression and model of the mouth, and the initial stages of making a denture comprise taking an impression by using plaster of Paris or an equivalent compound that hardens quickly while still in the mouth. This cast serves to make a wax model of the baseplate which is fitted with artificial teeth on the side remote from the jaw, in an order simulating the shape of the original denture of the patient. In the case that all teeth are missing, an upper and a lower denture are prepared on wax baseplates which are, after complete adaptation to the shape of the supporting parts, placed into an articulator which is adjusted by the dentist to simulate the relative movement of the jaws. In case some teeth are present in the jaw, the model dentures are positioned on a model of the gums which includes the remaining teeth which is similarly placed in the articulator.

By moving the denture models in accordance with the hinge movement of the articulator the teeth in the upper and the lower baseplate can be adjusted in their proper relation, so that their ultimate position in the mouth will permit proper chewing. As will be seen later, the use of the articulator is not perfect, and proper fit can only be obtained by grinding the teeth of the ready denture.

After the denture wax model has been tried out in the mouth of the patient, each denture is enclosed in a mold of plaster of Paris or an equivalent material, the mold is heated and the molten wax is allowed to flow out of the mold cavity until no trace of wax remains, while the teeth are embedded in the mold material and held therein firmly. The mold is then filled with liquid base plate material such as methylacrylate which encloses the bases of the teeth and hardens around the teeth and in the mold. After complete hardening the mold is broken open and the completed denture is extracted.

The denture is fitted into the patient's mouth, and he is asked to make masticating movements which indicate the spots which are too high and which have to be ground down. This is a lengthy operation, and it takes a long time until the teeth are finally ground down to a perfect chewing fit.

It will be understood that the grinding operation is only necessary in respect of the lateral teeth, i.e. premolars and molars, while the frontal teeth overlap during chewing and are only used for cutting the food initially.

It is the main object of the present invention to shorten the time needed for fitting dentures in the mouth, and thereby to facilitate the work of the dentists, by obviating the gradual grinding of the surface of the lateral teeth, in order to obtain a perfect chewing fit.

SUMMARY OF THE INVENTION

Production of an artificial denture in accordance with the present invention comprises the following steps: producing a baseplate of wax or equivalent material for the upper and/or lower denture in the conventional manner, which are to serve as patterns for eventual casting of the dentures; inserting a full set of artificial teeth in the baseplate of either the upper or the lower denture; inserting into the baseplate of the opposite denture the required number of artificial frontal teeth and the required number of artificial lateral teeth of tubular configuration, the latter teeth being characterized by the fact that their outer surface is anatomically correct and that their inside is hollow; placing the wax baseplates into the respective upper and lower jaw of a conventional articulator and adjusting the position of the lateral teeth in the base plates in such a manner that they correspond with the lateral teeth of the opposite denture and that each tooth forms at least one solid contact point with the teeth of the opposite denture; adjusting the incisor pin of the articulator so as to leave a space of about 0.5 mm between the cuspids and let the wax harden; filling the hollow spaces of the tubular teeth with wax to overflow, after hardening of the baseplate; moving the articulator in all directions so as to imitate mastication, whereby the wax protruding out of the tubular teeth will be removed until the upper wax surface is smoothed; removing the two denture patterns from the articulator and placing them into the mouth of the patient, letting him make masticating motions, whereby superfluous wax is removed until the respective contact points come into actual contact; roughening the now-smoothed upper surfaces of the wax fillings in the tubular teeth in the form of fissures as existing in natural teeth; making casting molds in the conventional manner, removing the wax out of the molds by melting and filling the thus created cavity with a plastic material of conventional composition, in liquid state, such as methylacrylate, whereby teeth-colored material is poured into the hollow spaces of the tubular teeth and gum-colored material into the remaining cavity, forming the gums; the ready cast dentures are now cured in the conventional manner.

The tubular teeth may be single units, or up to four teeth may be connected to each other to form a continuous row. Teeth of different color and hue, shape and size have to be chosen to suit various patients.

It is also noted that the method lends itself to the manufacture of complete or partial dentures, dependent upon whether all or only part of the natural teeth are missing in the upper and/or lower jaw.

From the above it will be understood that either the upper or the lower denture is fitted with a full set of artificial, conventional teeth, while the opposite denture contains conventional frontal teeth and lateral tubular teeth.

The tubular teeth can be manufactured as a serial product by a similar method as that used in the manufacture of solid artificial teeth, in different shapes and hues, having identical hardness and strength as the presently produced artificial teeth.

If necessary the surfaces of the tubular teeth may be cast in gold or be filled with conventional teeth stopping material such as amalgam or a composite material used in the stopping of decayed teeth.

SHORT DESCRIPTION OF THE DRAWINGS

DESCRIPTION OF THE METHOD

Figure 1:
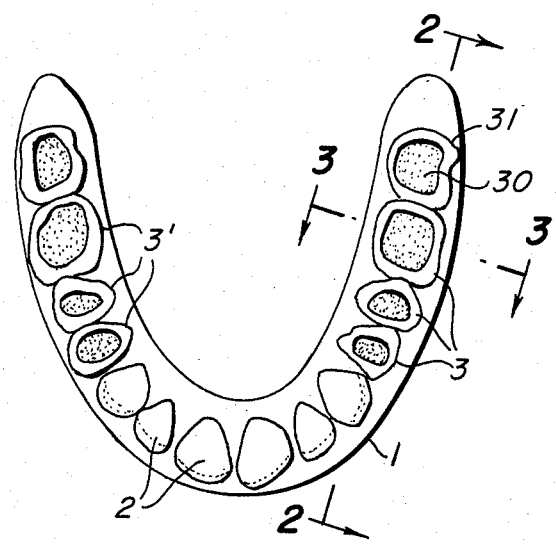
FIG. 1 is a plan view of a baseplate for a lower jaw provided with tubular lateral teeth on both sides, ready for filling the cavities in the teeth with wax.
Figure 2:
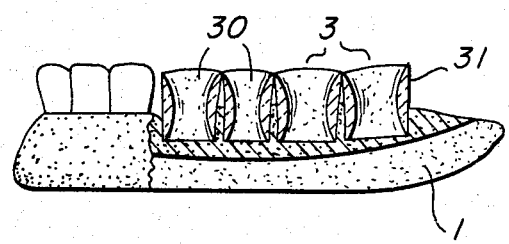
FIG. 2 is a section through the tubular teeth of the baseplate of FIG. 1, along the line A—A.
Figure 3:
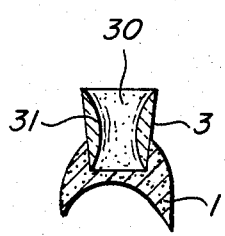
FIG. 3 is a section through one of the tubular teeth of FIG. 1, along the line B—B.
Figure 4:
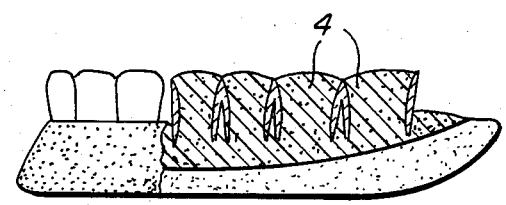
FIG. 4 is the section of FIG. 1, wherein the tubular teeth have been filled with wax, before positioning the denture into an articulator.

With reference to FIGS. 1, 2 and 3 of the drawings a denture baseplate 1 of wax contains six frontal teeth 2 and four lateral teeth 3, 3' on each side, which are embedded in the wax material to a certain depth so as to be firmly held in the base plate. The four lateral teeth on each side are each provided with an anatomically true outer contour and are hollowed out (30), leaving a relatively thin wall 31. While the wax is still pliable the baseplate is positioned on the gum-shaped bed of an articulator, and the opposite denture, in the present case the upper provided with a complete set of solid teeth, is placed into the movable upper portion of the articulator. The lateral teeth in either of the dentures are now respectively raised or lowered in the wax bed, until each tooth contacts the opposite tooth in at least one point, the so-called contact point. The dentures are now separated from each other by adjustment of the incisor pin of the actuator so as to leave a gap of about 0.5 mm between them. The actuator is now opened, i.e., the upper denture is raised, and the tubular teeth of the lower denture are filled with wax (4) which extends above their upper rim as shown in FIG. 4. The articulator is closed again and its upper part containing the upper jaw denture is moved so as to simulate the masticating motion of the jaws; this movement serves to remove superfluous wax from the top of the teeth by the rubbing action of the solid teeth in the upper denture. After the wax surface has thus been reduced and smoothed, it is roughened again by means of a hand tool, so as to present a natural teeth surface. The two dentures are placed in the mouth of the patient whose chewing movements remove an additional quantity of wax, the remaining surface corresponding to the final shape of the ideal denture which is up to now formed by repeated grinding off projecting portions of the ready-cast denture.

The wax denture is now removed from the patient's mouth and is enclosed in a mold in a known manner. The mold is heated, melting the wax which flows out and leaves a cavity corresponding to the shape of the baseplate and the hollow portions of the tubular teeth, while the artificial teeth, both the frontal teeth and the hollow tubular teeth are firmly embedded in the mold material.

The denture is cast by pouring liquid plastic material into the mold cavity, initially a tooth-colored material filling the hollow teeth, and subsequently a gum-colored material filling the baseplate cavity.

The denture is removed from the mold which is broken open, the denture is cleaned and smoothed, and will now fit the patient's mouth without requiring further adjusting of the bite by grinding.

The same procedure is carried out in respect of the upper denture, if such denture is required for the upper jaw.

The method, in the foregoing, has been described in respect of a denture for the lower jaw, but it will be understood that the same applies to the upper jaw as well, dependent on the state and the number of teeth remaining in either jaw.

In the foregoing the four lateral tubular teeth are shown to be connected to form a set, however, the invention is not limited to this form, but may comprise the fitting of separate teeth into the baseplate, or from two to three teeth to be jointed into one unit.

In respect to partial dentures, only one or two tubular teeth may be required, and the same method may be used in producing partial dentures.

The tubular teeth are manufactured by a similar method as solid artificial teeth, except in the case that up to four teeth are interconnected, when a combined mold is required. Different shapes and hues are provided as with solid teeth, and it will be understood that tubular teeth will have identical hardness and strength as solid teeth.

In certain cases, if the patient so wishes, the upper end of one or more tubular teeth may be filled with gold, amalgam or any other dental material, which would simulate these teeth to natural teeth treated by the dentist for caries.

I claim:

1. A method of manufacturing an artificial denture by implanting lateral tubular teeth in the upper or the lower denture, the method comprising producing a baseplate for the upper and/or lower denture to serve as patterns for casting of the dentures; fastening by means of wax or an equivalent a full set of artificial teeth to the baseplate of one of said dentures; fastening by means of wax or an equivalent to the baseplate of the other of said dentures a predetermined number of artificial frontal teeth and a predetermined number of lateral teeth, said lateral teeth having an outer surface which is anatomically correct and being hollow; placing the baseplates into respective upper and lower jaws of an articulator and adjusting the position of the lateral teeth in the base plates so that they correspond with the lateral teeth of the opposite denture and so that each tooth forms at least one solid contact point with the teeth of the opposite denture; adjusting said articulator so as to leave a space between the cuspids and allowing the wax to harden; after hardening of the wax filling the hollow spaces of said lateral teeth with wax to overflow; moving said articulator so as to imitate mastication, whereby the wax protruding out of the lateral teeth is removed until the upper wax surface is smoothed; removing said dentures from said articulator and placing said dentures into the mouth of the intended user, allowing the intended user to make masticating motions for removing superfluous wax until the respective contact points come into actual contact; roughening the smoothed upper surfaces of the wax fillings in said lateral teeth into the form of fissures corresponding to natural teeth; removing the wax by melting, and filling the thus created cavity with a plastic material in liquid state; and curing the plastic material.

2. The method of claim 1, wherein said tubular teeth are manufactured from a plastic dental material such as methylacrylate.

3. The method of claim 2, wherein from two to four tubular teeth are connected to each other to form one solid unit.

4. The method of claim 1, wherein said mold is filled with liquid plastic material, comprising pouring a first quantity of tooth-colored material filling said tubular teeth and a second quantity of gum-colored material filling the cavity corresponding to said baseplate.

5. The method of claim 1, wherein the contact surfaces of said tubular teeth are filled with a metal such as gold or an amalgam.

* * * * *